(12) United States Patent
Rabinowitz

(10) Patent No.: US 7,005,154 B2
(45) Date of Patent: Feb. 28, 2006

(54) DIETARY FIBER, PROCESS FOR PREPARING IT, AND AUGMENTED DIETARY FIBER FROM ALMOND HULLS

(76) Inventor: Israel N. Rabinowitz, 2534 Foothill Rd., Santa Barbara, CA (US) 93105

( * ) Notice: Subject to any disclaimer, the term of this patent is extended or adjusted under 35 U.S.C. 154(b) by 455 days.

(21) Appl. No.: 10/202,506

(22) Filed: Jul. 24, 2002

(65) Prior Publication Data

US 2004/0018255 A1  Jan. 29, 2004

(51) Int. Cl.
*A23L 1/015* (2006.01)
(52) U.S. Cl. .................. 426/430; 426/489; 426/52
(58) Field of Classification Search ........... 426/431, 426/430, 482, 489, 52, 51, 629, 655; 424/735, 424/776; 210/650
See application file for complete search history.

(56) References Cited

U.S. PATENT DOCUMENTS

| 4,997,489 A | | 3/1991 | Rabinowitz | |
|---|---|---|---|---|
| 5,064,762 A | | 11/1991 | Rabinowitz | |
| 5,160,756 A | | 11/1992 | Rabinowitz | |
| 5,624,699 A | * | 4/1997 | Lang | 426/425 |
| 5,626,847 A | * | 5/1997 | Agrawal et al. | 424/750 |
| 6,716,465 B1 | * | 4/2004 | Rabinowitz | 426/431 |

* cited by examiner

*Primary Examiner*—Keith Hendricks
(74) *Attorney, Agent, or Firm*—Donald D. Mon

(57) ABSTRACT

Dietary fiber derived from almond hulls (the dried mesocarp of the senescent almond) enhanced by the treatment with yeasts to remove sugars.

10 Claims, 2 Drawing Sheets

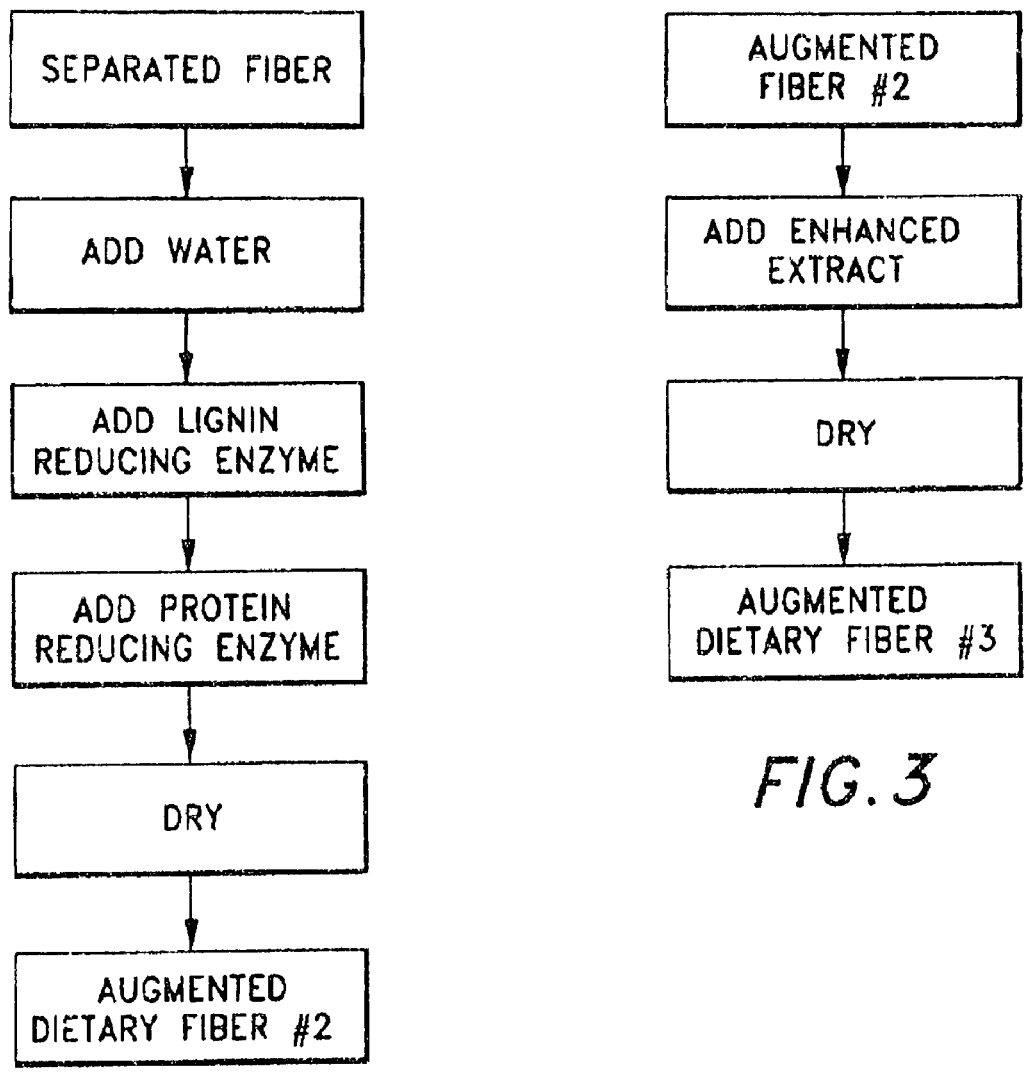

DIETARY FIBER, PROCESS FOR PREPARING IT, AND AUGMENTED DIETARY FIBER FROM ALMOND HULLS

FIELD OF THE INVENTION

Dietary fiber, a process for preparing it, and augmented dietary fiber, the fiber being derived from the fruit of the sweet almond, this fruit when dried frequently being called "almond hulls".

BACKGROUND OF THE INVENTION

The sweet almond (prunus amygdalus) belongs to a family of fruit trees which includes the apricot, the peach and the plum. Dietary habits relating to the fruits of these trees differ markedly. As a consequence, the flesh part of the apricot, of the peach and of the plum is the portion which is consumed—either as a fresh, dried, or preserved product. The plum is often dried to a condition called a prune. Prune juice is the water extract of the dried prune. In every culture, the inside of the apricot, peach or plum is discarded. Only the outer flesh (the mesocarp) is recovered and consumed in some way.

The almond has had a remarkably different history. In some cultures, particularly in the Mediterranean, the flesh is consumed while it is a fresh product, and is greatly enjoyed. However, in most of the world, and especially in the United States, the important crop is the inside nut. The flesh part is only rarely consumed as such, and not as a major crop. Instead, the almond fruit is permitted to remain on the tree for a very extended time well into senescence. The flesh part (mesocarp) dries to a moisture content of between about 5%–29% by weight, preferably about 10% while still on the tree.

During this time while still on the tree, the almond mesocarp has entered a period of biological senescence. After collection from the tree and separation from the nut meat, it is regarded as a low-value product, generally called the "almond hull". This is in contrast with other fruits, which are harvested before senescence has set in and have their own sets of taste and content. In their situations, the nuts are discarded and the mesocarp is eaten while in what can be regarded as a youthful phase. However, for almonds, the nut is the crop, and the mesocarp is used as a fuel to be burned, or is fed to cattle as a feed supplement. It is an underappreciated fact that almond hulls contain useful fiber and various phytochemicals useful as dietary supplements.

It is known that almond hulls contain inositol, sugars, and various other compounds including lignin, but the inventor herein is unaware of any prior effort (certainly not a commercially successful effort) not only to obtain useful dietary fiber, but also to prepare augmented almond hull dietary fiber, relying principally on the inherent contents of the almond hull itself for its ultimate compositions, and on benign processes for doing it.

There has been found a relationship between human populations which consume low fiber diets and a higher incidence of gastrointestinal (GI) cancers in those populations. The scientific and medical literature on this subject is now huge, and growing. Considerably more is now known about the chemical composition of "dietary fiber" and its real and possible roles in prevention of several diseases, primarily afflicting the ageing, including cancer, cardiovascular disease, and diabetes, in addition to a few dozen diseases which center on the GI tract, such as Crohn's disease, ulcerative colitis, and colorectal cancer. In view of this increased knowledge of the basic chemistry of dietary fiber, and its putative medical benefits, the United States Food and Drug Administration is currently considering an update of the scientific definition of dietary fiber (frequently hereinafter referred to as "DF").

One of the first definitions of DF, still quite serviceable is: Dietary Fiber (DF) consists of the remnants of edible plant cells, polysaccharides, lignin, and associated substances resistant to hydrolysis and digestion by the alimentary (i.e GI tract) enzymes of humans. The reference to human enzymes is significant, because since this definition was proposed, it is now appreciated that the normal microbial population (bacteria, yeasts, and fungi) of the human GI tract, play important roles in maintenance of health. These microbes have the enzyme capability to digest selected fractions of DF, to the benefit of their hosts.

The new FDA definition perhaps to be announced in 2002, will be important, as it will directly impact nutritional labeling of foods and supplements, and regulatory matters relating to allowable health claims. DF's derived from cereals have been shown to beneficially affect laxation, by virtue of both their insoluble polysaccharide fraction, and soluble polysaccharide fraction, via different mechanisms for the two different fractions. Further, specific sub-fractions of DF polysaccharides have been shown to be responsible for enhanced laxation. It appears that fruit and vegetable DF, may have greater prophylactic activity against GI cancers, than do cereals DF. This activity, however, may also be due at least in part, to the antioxidant actions of fruit and vegetable polyphenolic compounds, such as flavonoids, lignans, anthyocyanidins.

It is an object of this invention, to make use of a unique augmented DF, achieved by proper processing of currently under-utilized fruit, which is actually the waste product of the commercial farming and harvesting of a different component of this fruit. Further, the DF which can be recovered from this fruit, can also be augmented with other phytochemical components of the fruit, in novel ways, so as to increase the beneficial DF and prebiotic actives of this augmented DF. A prebiotic is a food or supplement which contributes to a healthy intestinal microbial population.

The almond has a unique mixture of polysaccharides (e.g. cellulose, hemicelluloses, etc.) sugars, and polyphenolics (e.g. flavonoids, anthocyanidins, lignans, and lignins), and other organics and minerals content. It differs from other harvested fruits by having undergone a significantly different biochemical anabolic and catabolic process while still on the tree. The inventor herein has learned that, after comminution of the dried fruit (the almond hull) to a fine or coarse powder, the dried fruit can be rehydrated with water, allowing separation of water soluble sugars, and other low molecular weight organics, from a remaining, predominantly higher molecular weight polysaccharide plus polyphenolic solids residue. Lower molecular weight sugars, and other organics (including flavonoids, terpenes, anthocyanidins, lignans), can also be separated from the fruit via, for example, supercritical carbon dioxide extraction, or via water plus organic solvent mixtures leaving a similar remaining higher molecular weight residue. Extraction techniques using only water is preferred for both food safety and process economics advantages.

BRIEF DESCRIPTION OF THE INVENTION

This invention begins with utilization of clean, dry almond hulls comminuted to a fine or coarse powder. This material is then rehydrated with water. This enables the separation of the water soluble sugars and lower weight organics from the remaining predominantly higher molecular weight polysaccharide plus phenolic solids residue. This provides a "water extract" of the solubles.

According to a first embodiment of this invention the water extract is treated with a yeast which functions to remove the sugars (which are an undesirable constituent of a fiber product), and to increase the inositol content by weight. The yeast solids are filtered out, and the effluent water solution remaining is concentrated and returned to the fiber, which is then dewatered and dried, and provided an augmented DF.

According to a second embodiment of the invention the said residue is dried and reduced to small particles, and a lignin-reducing enzyme is added to it while in an aqueous suspension. This results in a DF which is increased in lignans. It is dried to form augmented powder.

According to a third embodiment of the invention, the enzyme-treated suspension of the second embodiment may have added to it the yeast-treated solution from the first embodiment, thereby creating a third embodiment which enjoys the advantages of both of the first two embodiments.

The above and other features of this invention will be fully understood from the following detailed description and the accompanying drawings, in which:

BRIEF DESCRIPTION OF THE DRAWINGS

FIG. 2 is a flow diagram for the second embodiment;
and
FIG. 3 is a flow diagram for the third embodiment.

DETAILED DESCRIPTION OF THE INVENTION

Figure 1:
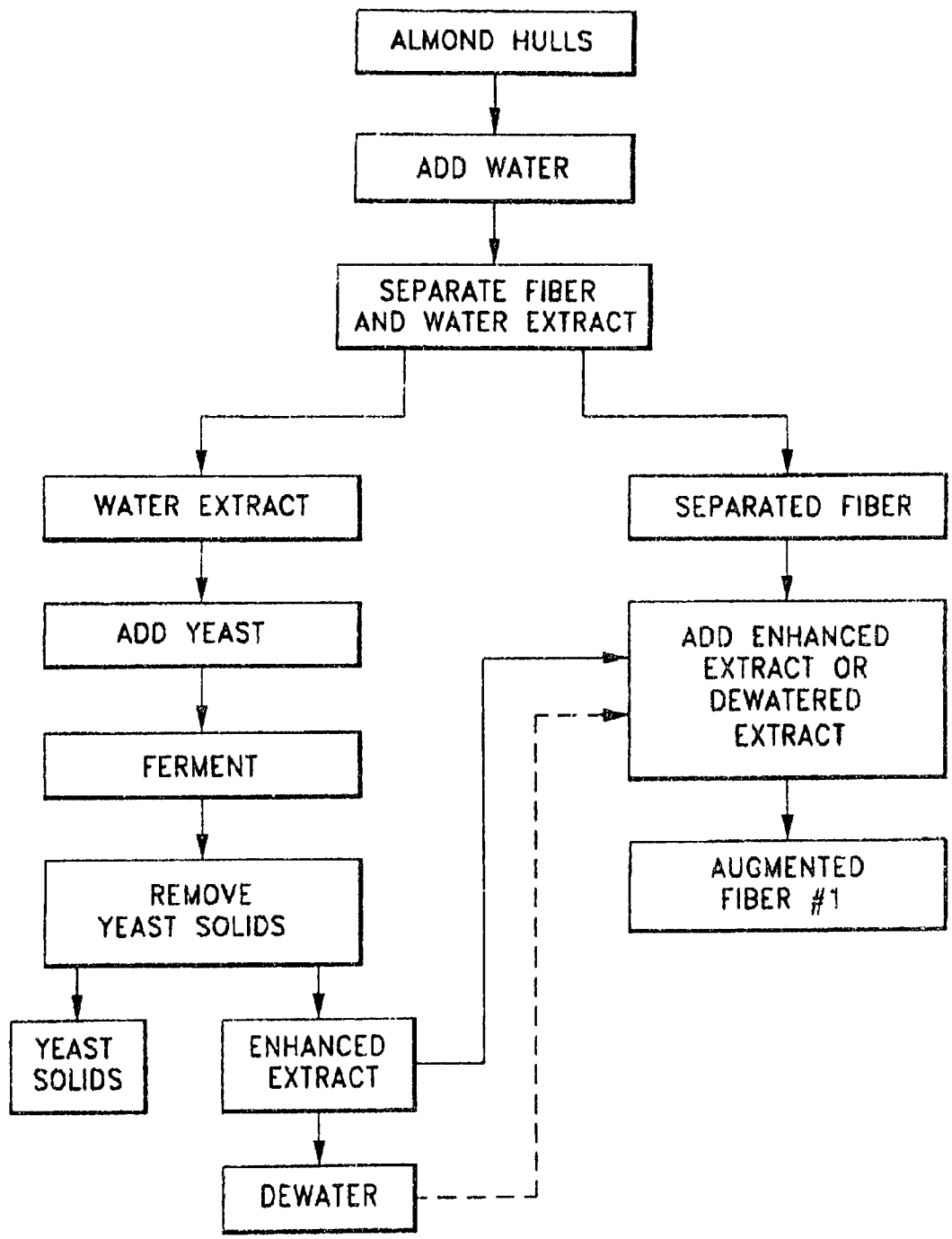
FIG. 1 is an flow diagram for the first embodiment.

In all of the embodiments of this invention, one begins with clean almond hulls ground to a suitable size for water extraction of the solubles in them.

The dried hulls are rehydrated with water 11, allowing separation of water soluble sugars, and other low molecular weight organics, from a remaining, predominantly higher molecular. weight polysaccharide plus polyphenolic solids residue. Lower molecular weight sugars, and other organics (including flavonoids, terpenes, anthocyanidins, lignans) can later be separated from the fruit via, for example supercritical carbon dioxide extraction, or via water plus organic solvent mixtures leaving a similar remaining higher molecular weight residue. Extraction techniques using only water are preferred for both food safety and process economics, advantages.

If water extraction of lower molecular weight solubles is followed, using appropriate counter current techniques, the extraction of solubles may be aided, during the counter current step by addition of commercially available "juicing" enzymes such as pectinases, amylases, proteases. Also during the counter current step, more specific phosphatases, or viable yeasts possessing phosphatases activity may be added, thereby reducing total phytic acid content, and increasing inositol phosphates content. Suitable yeast could be selected from the several strains of wine or baking *S. cerevisiae* yeasts, or selected strains of *S. pombe*, or strains of *Schwannionyces Castelli*, or *S. Boulardii*. Fungi of *Aspergillus* genus are likewise suitable, as well as selected bacterial strains from among *subtilis, pseudomonas,* and *klebsiella*. Suitable bacterial and fungal strains thus grown on the almond fruit extract, may be harvested for probiotic uses in both animal feed, and human supplement, usages in disease treatment, as for example, for the uses of *S. boulardii*.

After separation of low molecular weight solubles from the residue material, the residue (separated fiber) may be de watered from its approximately 20% solids content, to approximately 35% solids content, and then dried to a final approximately 89%–95% solids content. The dewatering and drying steps are achieved via well known processes employed in the sugar, juice and starch processing industries.

The resulting dried fruit fiber thus prepared is found to be an excellent food fiber, suitable for many applications, but is as yet not augmented. With no further processing, the tan colored fiber is found, for example, to be an excellent replacement, or extender for cacao, in chocolate containing products, i.e. it can help in production of low calorie, high fiber, "chocolate" products. If a tan color is not acceptable for other applications, the fiber may be readily bleached to a white color with commercially available food bleaching agents, such as peroxides. To produce a totally bland tasting fiber, the fiber may be further treated with dilute alkali, or sodium carbonate, or sodium sesquicarbonate, with or without also adding bleaching agents. Both lightly colored, and the bleached solids, are dried to approximately 6% moisture content, yielding a very high total DF product, with celluosics and hemicellulosics comprising some 73% and lignin some 14% of a total 87%±1% DF product. The polysaccharide fraction of the DF is approximately 60% water insoluble, and approximately 12% water soluble, comparing favorably with the current suggested optimal dietary reference intake of 75% insoluble and 25% soluble DF, characteristic of, e.g. oat and wheat cereal DF.

The almond fruit DF has the additional benefit of high lignin content, characteristic of fruit DF. The almond fruit DF therefore combines the beneficial features of both cereal and fruit DF, in one product. Further, the almond fruit DF contains in its soluble polysaccharaide fraction a very high molar ratio of arabinose to xylose to galactose sugars, therefore closely resembling the arabinan-xylan-galactan composition of plantago ovata, or "psyllium" fiber product, recently shown to be efficacious for laxation because of this sugar composition. Also, the high molar concentration of galactose in both the water soluble, and water insoluble polysaccharide fractions, is advantageous, as it has been recently demonstrated that galactose in DF plays a key role in prevention of GI cancer. For both food supplement uses, as well as for prebiotic activity, the water holding capacity of the almond fruit DF, which is in excess of 10 g water per 1 g of DF is advantageous.

According to this invention, the almond fruit DF products 13 thus far described, above, can according to this invention be augmented with additional selected almond fruit components, to produce a DF with superior prebiotic and antioxidant functionalities. The augmented DF products are designed in light of recent basic research emphasizing the complex and beneficial relationship between intestinal microbial polulations and the epithelial and mucus cells lining the lumen of the large intestine and colon, which impact immunological defense mechanisms and support the main functions of the intestine and colon, which are salt and water absorption control.

A key player in all of these mechanisms is the metal calcium. Calcium is perhaps the most important, certainly most ubiquitous, second cell "messenger" in physiological signal transduction processes, involved in all cell functions, starting with fertilization of egg for reproduction, to programmed and necessary, cell death, or apoptosis. Very recently added to the list of Calcium roles in signal transduction is its role in signaling in colonic epithelial and musosal cells, regulating cell differentiation, reduced call growth, and reduced risk of colorectal cancer.

It is also known that in many of the signal transduction roles of Calcium, metabolites of inositol, the inositol phosphates, aid in the action of Calcium, and this is now seen to be the case in the cells lining the lumen of the large intestine and colon. It has also recently been suggested that the major beneficial site of activity of the food phytochemical antioxidants is the large intestine and colon.

The heretofore largely ignored component of DF, the lignin (and lignan) fraction, have recently been demonstrated to aid in chemoprevention of GI cancers. Lastly, inositol itself has long been recognized as an essential vitamin for bacteria and yeast. In view of these new findings, the three new augmented almond fruit DF products described herein have been designed. The concentrated syrup of the water extract described above at 75 degrees to 85 degrees Brix can contain approximately 100–300 mg./ml. of inositol, and as an indicator of total flavonoid content, approximately 60 ug/ml. of quercitin, in both free and glycosidically bound from. Variable concentrations are primarily due to mix of almond fruit varietals that are used. There will also be inter alia, approximately 150 mg./ml. of sorbitol, which as a polyol has beneficial effect in water retention and laxation in the large intestine and colon.

AUGMENTED DF 1

A beneficial augmented DF composition referred herein as augmented DF #1, will be composed of, for example, 100 ml. of 77 degrees Brix syrup plus 100 grams of unbleached DF described above, plus 1–5 grams of micron sized $C_aCO_3$ or Ca-lactate, of Ca-gluconate, or some other Calcium salt of an organic acid, such as calcium-citrate.

This composition is diluted with water to between 30%–70% total solids content, stirred to a homogeneous suspension, and then spray dried to approximately 5%–10% moisture, 100–500 u particle size. The calcium acts as both a source of calcium, and as an excipient for the spray dried powder. Inositol is present to facilitate calcium activity in the GI tract, and as a vitamin for resident biota.

The effective encapsulation of inositol in the DF insures that most of the inositol will reach the large intestine and colon, rather than being absorbed from the small intestine, where it would normally be absorbed in the absence of encapsulation. Thus inositol, calcium, flavonoids, sorbitol, and DF are all targeted and delivered specifically to the large intestine and colon, which is the desired delivery locus for an effective prebiotic DF. An example of such an augmented DF formulation would contain, per 100 grams of DF, at 6% moisture, 9 grams of inositol, 6 mg, of quercitin, 2 mg. other mixed polyphenolics, 1.8 grams $C_aCO_3$.

For perspective about the significance of these concentrations delivered to a targeted site, we see that, for example, oral ingestion of 720 mg. of total anthocyannis (elderberry extract), with four human subjects, resulted in an average blood plasma concentration of the glycated molecules of 97 nmol/L (20). Assuming average total blood volume of 5 liters, this is approximately 30 ug/ml. available to be distributed to many different final organ sites for absorption.

AUGMENTED ALMOND FRUIT DF 2

Additional cancer chemoprevention may be effected by proving higher concentrations of lignin fractions, such as lignans, made available to the large intestine and colon. Little is known about lignin degrading enzymes in the human gut, but it is known that there is low level activity of one such enzyme, ferulic acid esterase (FAE) in the human gut. Therefore (see FIG. 2) almond fruit DF, in an aqueous suspension of 100 u–500 u particles, approximately 30% total solids, is exposed to an ferulic acid esterase (FAE) enzyme of high activity, at 37 degrees C., with good stirring for 5 to 24 hours. The enzyme will be used in the ratio of approximately 0.5 to 1.0 Kg per 1000 Kg. of total DF solids. At the end of the FAE enzyme treatment, a human food grade protease enzyme, such as papain or bromelain, will be added to the reaction mixture for 30–60 minutes at temperature between 55 degrees to 70 degrees C. to reduce the FAE protein to amino acids and peptides, and the DF suspension will then be spray dried to a dry powder, as described above. Additional benefit of the FAE treatment is breaking of bonds between lignin and polysaccharide, thus exposing more of the arabinan-xylan galactan polymer region for effective action.

AUGMENTED ALMOND FRUIT DF #2.

The augmented almond fruit DF #2 will be used as the DF to be mixed with inositol, sorbitol, flavonoids, as described for augmented DF #1 above.

For the latter two augmented dietary fiber preparations, DF 2 and DF 3, the preparations will contain phytic acid (inositol -6 phosphate) and lower phosphorylated inositol (e.g. inositol -5 phosphate, inositol -4 phosphate down to inositol -1 phosphate) which have been shown to possess antineoplastic activity in the colon. They will be present in nanogram to microgram amounts, dependent primarily upon a mix of varietals used in the initial extraction process. Lignans and higher molecular weight lignin fractions will likewise be present in nanogram to microgram amounts, dependent upon varietal mix initially extracted.

This invention is not to be limited by the embodiments shown in the drawings and described in the description, which are given by way of example and not of limitation, but only in accordance with the scope of the appended claims:

I claim:

1. An augmented dietary fiber derived from almond hulls produced by the following process:
   a. subjecting almond hulls to aqueous extraction, whereby to produce fiber solids and an aqueous extract of soluble constituents of said almond hulls, and removing said aqueous extract from said fiber solids;
   b. combining said aqueous extract and a yeast, said yeast being of a type that consumes sugars dissolved in said extract, thereby to remove said sugar;
   c. removing yeast solids from the product of step b, whereby to produce an enhanced extract in an amount proportional to the amount of almond hulls from which it is derived;
   d. combining said fiber solids and at least some of said enhanced extract to form an augmented dietary fiber.

2. A dietary fiber according to claim 1 in which an amount of enhanced extract in excess of the respective derived amount is added to the fiber.

3. A dietary fiber according to claim 1 in which said enhanced extract and solids are joined in step d in an aqueous suspension, and said suspension is then dried to produce a dried augmented dietary fiber.

4. A dietary fiber according to claim 1 in which said enhanced extract is evaporated to a concentrate before being added to the fiber in step d.

5. The process of preparing an augmented dietary fiber comprising the following steps:
   a. subjecting almond hulls containing lignin to aqueous extraction, whereby to produce fiber solids and an aqueous extract of soluble constituents of said almond hulls in an aqueous suspension;
   b. combining said fiber solids first with an enzyme that hydrolyzes the lignin in the fiber;
   c. followed by enzymes that digest remaining proteins to amino acids and peptides; and
   d. drying said suspension.

6. The process according to claim 5 in which a calcium salt is added to said fiber solids.

7. An augmented dietary fiber derived from almond hulls produced by the following process:
   a. subjecting almond hulls containing lignin to aqueous extraction, whereby to produce fiber solids and an aqueous extract of soluble constituents of said almond hulls, and removing said aqueous extract from said fiber solids;
   b. combining said fiber solids and an enzyme capable of reducing lignins to lignans in an aqueous environment, and reacting them;
   c. adding protein digesting enzymes to reduce remaining proteins to amino acids and peptides; and
   d. drying the product of step c, thereby to form an augmented dietary fiber.

8. The process of preparing an augmented dietary fiber comprising:
   a. subjecting almond hulls to aqueous extraction, whereby to produce fiber solids and an aqueous extract of soluble constituents of said almond hulls, and removing said aqueous extract from said fiber solids;
   b. combining said aqueous extract and a yeast, said yeast being of a type to consume sugars dissolved in said extract;
   c. removing yeast solids from the product of step b, whereby to produce an enhanced extract in an amount proportional to the amount of almond hulls from which it is derived;
   d. combining said fiber solids and at least some of the enhanced extract to form an augmented dietary fiber.

9. A process according to claim 8 in which an amount of enhanced extract in excess of the respective derived amount is added to the fiber.

10. An augmented dietary fiber derived from almond hulls produced by combining the augmented dietary fibers of claims 1 and 7.

* * * * *